United States Patent [19]
Fattom et al.

[11] Patent Number: 5,866,140
[45] Date of Patent: Feb. 2, 1999

[54] **TYPE I SURFACE ANTIGEN ASSOCIATED WITH *STAPHYLOCOCCUS EPIDERMIDIS***

[75] Inventors: Ali Ibrahim Fattom, Rockville, Md.; Walter W. Karakawa, deceased, late of Pennsylvania Furnace, Pa., by Walter W. Karakawa, legal representative; D. Craig Wright, Gaithersburg, Md.

[73] Assignee: Nabi, Boca Raton, Fla.

[21] Appl. No.: 361,821

[22] Filed: Dec. 22, 1994

Related U.S. Application Data

[63] Continuation of Ser. No. 142,117, Oct. 28, 1993, abandoned, which is a continuation of Ser. No. 796,252, Nov. 22, 1991, abandoned.

[51] Int. Cl.$^6$ ........................ A61K 39/085; A61K 39/00; A61K 45/00; A61K 39/02
[52] U.S. Cl. ................................. 424/243.1; 424/184.1; 424/279.1; 424/282.1; 424/234.1
[58] Field of Search ............................. 424/184.1, 243.1, 424/279.1, 184, 282.1, 234.1

[56] References Cited

U.S. PATENT DOCUMENTS

| | | | |
|---|---|---|---|
| 4,197,290 | 4/1980 | Yoshida | 424/92 |
| 4,902,616 | 2/1990 | Fournier et al. | 435/101 |
| 5,055,455 | 10/1991 | Pier | 514/54 |
| 5,097,020 | 3/1992 | Anderson | 530/403 |

FOREIGN PATENT DOCUMENTS

| | | |
|---|---|---|
| 0 302 781 | 2/1989 | European Pat. Off. . |
| WO 90-3398 | 4/1990 | WIPO . |

OTHER PUBLICATIONS

Kijima et al., "Antibody to the Capsular Polysaccharide/Adhesin Protects Rabbits against Catheter–Related Bacteremia . . . ", *Jnl. of Inf. Dis.*, 162:435–441 (1990).

Yoshida et al., "Isolation of an Encapsulated Strain of *Staphylococcus epidermidis*", *The Society for Applied Bacteriology*, 47:299–301 (1979).

Tojo et al., "Isolation and Characterization of a Capsular Polysaccharide Adhesin from *Staphylococcus epidermis*", *Jnl. of Infectious Diseases*, 157:713–722 (1988).

Archer, "*Staphylococcus epidermis*: The organism, its diseases, and treatment", *Corr. Clin. Topics Infect. Dis.*, pp. 25–48 (1984).

Ichiman et al., "The Relationship of Capsular–type of *Staphylococcus epidermis* to Virulence and Induction . . . ", *Jnl. of Applied Bacteriology*, 51:229–241 (1981).

Ichiman et al., *Jnl. of Applied Bacteriology*, 71:176–181 (1991).

Ichiman et al., "Protective antibodies in human sera against encapsulated strains of *Staphylococcus epidermis*", *Jnl. of Applied Bacteriology*, 63:165–169 (1987).

Robbins et al., "Prevention of Invasive Bacterial Diseases by Immunization with Polysaccharide Protein Conjugates", *Current Topics in Microbiology and Immunology*, 146:169–180 (1989).

Nelles et al., *Infect. Imm.*, 49:14–18 (1985).

Fattom et al., *Infect. & Immunity*, 58:2367–2374 (1990).

McDonald et al., "Immunochemical Analysis of a Uronic Acid Polymer of *Staphylococcus epidermis*, Strain 53", *Jnl. of Immunology*, 105:389–395 (1970).

Aasen, et al., Antigenic Studies on *Staphylococcus Epidermidis*, Acta path. microbiol. Scand. Section B, 79:827–834 (1971).

Johnsen, et al., Studies on Polysaccharide C of *Staphylococcus Epidermidis* Acta path. microbiol. scand. Sect. B. 83:226–234 (1975).

Johnsen, et al., Studies on Polysaccharide C of *Staphylococcus Epidermidis* Acta path. microbiol. scand. Sect. B. 83:235–239 (1975).

Hussain, et al., Comparison of cell–wall teichoic acid with high–molecular–weight extracellular slime material from *Staphylococcus epidermidis*, J. Moc. Microbiol. vol. 5:368–375 (1992).

Endl, et al., Chemical composition and structure of cell wall teichoic acids of staphylococci, Arch Microbiol. 135:215–223 (1983).

*Primary Examiner*—Susan A. Loring
*Attorney, Agent, or Firm*—Foley & Lardner

[57] ABSTRACT

A process is disclosed for culturing clinical *Staphylococcus epidermidis* cells that reproducibly enables identification of a limited number of predominant serotypes. Two predominant serotypes common to most clinical cases of *S. epidermidis* have been identified and are denoted Type I and Type II. A particular polysaccharide surface antigen is associated with each of the Type I and Type II serotypes. The surface antigens can be used to provide active and passive immunization against *S. epidermidis* infection and to produce a hyperimmune immunoglobulin or antibodies for treatment of *S. epidermidis* infection.

10 Claims, No Drawings

TYPE I SURFACE ANTIGEN ASSOCIATED WITH *STAPHYLOCOCCUS EPIDERMIDIS*

This application is a continuation of application Ser. No. 08/142,117, filed Oct. 28, 1993, now abandoned, which is a continuation of application Ser. No. 07/796,252, filed Nov. 22, 1991, which is now abandoned.

BACKGROUND OF THE INVENTION

The present invention relates to particular serotypes of *Staphylococcus epidermidis*, to a method of identifying these serotypes, and to a vaccine produced using these surface antigens associated with these serotypes. The invention also relates to methods of active and passive immunization of humans and animals infected with or susceptible to infection with *Staphylococcus epidermidis*.

Coagulase-negative Staphylococcus infections are a leading cause of bacteremia in hospitalized patients. In particular, *S. epidermidis*, formally thought not to be a pathogen, has been discovered to be a significant factor in this bacteremia. Morbidity and mortality from *S. epidermidis* infection is especially high among patients requiring prosthetic medical devices. This is thought to be a result of slime produced by *S. epidermidis* which permits adherence to and colonization of these medical examples, e.g., catheters and heart valves.

Because the slime is thought to be the factor responsible for infection by *S. epidermidis*, attention has focused on those aspects of the surface which mediate attachment to foreign bodies. An extracellular slime has been identified by various researchers, and culture conditions promoting production of this slime have been used.

In addition to a focus on the slime produced by *S. epidermidis*, research to date has largely been directed toward a limited number of specific strains of the bacteria which have been isolated. Ichiman et al. studied three strains of *S. epidermidis*, which they cultured in Brain Heart Infusion (BHI) broth. Immunization of mice with cell surface polysaccharides from these cultured microorganisms were not effective, however, in providing protection to heterologous strains. Characterization of the surface polysaccharides which were isolated showed serological heterogeneity. Ichiman et al., *J. Appl. Bact.* 51: 229–241 (1981).

According to Ichiman, in order to be an effective vaccine for clinical use, each infective strain would have to isolated and a vaccine developed against each strain. This would be untenable from a practical standpoint.

SUMMARY OF THE INVENTION

It is therefore a primary object of the invention to provide a process for culturing clinical *S. epidermidis* cells that reproducibly enables identification of a limited number of predominant serotypes.

It is another object of the present invention to identify and characterize the predominant serotypes relating to clinical *S. epidermidis* infection.

It is a further object of the invention to provide an effective vaccine for clinical use against *S. epidermidis* infection.

It is yet another object of the invention to provide a vaccine which is effective against most clinically pathogenic strains of *S. epidermidis*.

It is a further object of the invention to prepare polyclonal antisera specific for surface antigens associated with clinical isolates of *S. epidermidis*.

It is another object of the invention to provide monoclonal antibodies to the surface antigens associated with the predominant serotypes of clinical *S. epidermidis,* which can be used to protect against or treat *S. epidermidis* infection.

It is yet another object of the invention to provide hyperimmune IVIG to protect against or treat *S. epidermidis* infection.

These and other objects according to the invention are achieved by a composition consisting essentially of at least one of a Type I and Type II surface antigen of *S. epidermidis*. A vaccine comprising this composition and a sterile, pharmaceutically-acceptable carrier is also provided. An immunostimulatory amount of this vaccine can be administered to a subject. This subject may already be infected with *S. epidermidis* when said vaccine is administered. Alternatively, the vaccine can be administered to a plasma donor, stimulating that donor to produce a hyperimmune globulin which contains antibodies directed against *S. epidermidis*. An immunostimulatory amount of this hyperimmune globulin can then be administered to a subject.

Also provided according to the present invention is a composition consisting essentially of antibodies that bind Type I or Type II surface antigens. In a preferred embodiment these antibodies are not obtained by a process comprising the step of providing a biological sample from a human subject infected with *S. epidermidis*. The antibody composition according to the invention may be a monoclonal antibody composition. Immunostimulatory amounts of antibody compositions according to the invention, particularly monoclonal antibody compositions, can be administered to a subject to prevent or treat *S. epidermidis* infection.

A serotyping kit for *S. epidermidis* cultures is provided which comprises antibodies specific to Type I surface antigen and antibodies specific to Type II surface antigen. In a preferred embodiment, the antibodies are monoclonal antibodies. A method of serotyping isolates of *S. epidermidis* is also provided, comprising the steps of growing cells of an isolate of *S. epidermidis* in an environment in which the level of available phosphate simulates the level of available phosphate in vivo; and mixing the cells with type-specific antibodies selected from the group consisting of anti-Type I specific antibodies and anti-Type II specific antibodies; and monitoring the mixture of cells and antibodies for agglutination.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

It has surprisingly been discovered according to the present invention that, by culturing *S. epidermidis* under conditions that minimize slime formation, and enhance production of capsular polysaccharides, a limited number of serotypes common to most clinical cases of *S. epidermidis* can be identified. More particularly, it has been found that more than 85% of clinical isolates display one of two predominant serotypes, denoted Type 1 and Type 2, respectively. It has been determined that the surface antigens responsible for the two serotypes are acidic polysaccharides, which contain aminouronic acids and other amino sugars. These polysaccharides are negatively charged, moving toward the positive pole in a countercurrent immunoelectrophoresis. They are also type-specific, that is, immunoprecipitation produces a single band with only the homologous-type antiserum.

The acidic polysaccharide antigens associated with each serotype can be obtained in recoverable amounts, from S. epidermidis isolates cultured, serotyped and purified pursuant to the protocols described herein, in substantially pure form. In particular, purified antigen contains less than 1% protein and less than 1% nucleic acids. A "recoverable" amount in this regard means that the isolated amount of the acidic polysaccharide is detectable by a methodology less sensitive than radiolabeling, such as an immunoassay, and can be subjected to further manipulations involving transfer of the acidic polysaccharide per se into solution.

A composition of the acidic polysaccharide antigen according to the present invention consists essentially of one or both of the acidic polysaccharide antigens associated with Type I and Type II, respectively. That is, such a composition must not contain any material that interferes with production of an immune response to the acidic polysaccharide epitopes when they are administered to a subject as a vaccine. In a preferred embodiment, the composition contains both acidic polysaccharide antigens according to the present invention.

Serotypes of S. epidermidis can be identified in clinical isolates grown on a medium that mimics, as nearly as possible, in vivo conditions. In particular, this medium should provide an environment in which the amount of available phosphate is low. Such a medium minimizes slime production by the bacteria and enhances production of capsular polysaccharide, particularly the acidic polysaccharides according to the present invention. This is in clear contrast to BHI broth and tryptic soy broth (TSP), the media commonly used in studies of S. epidermidis and ones that are high in available phosphate, having about 2.5 mg of phosphate per ml. These media enhance slime production. When grown on a medium simulating in vivo conditions, S. epidermidis will produce surface antigens that will not adhere to glass or plastics.

The preferred medium according to the present invention is a modified Columbia broth (Difco Laboratories, Detroit, Mich.), a medium in which the level of available phosphate is 76 $\mu$g/ml. Such a medium simulates the in vivo level of available phosphate in humans, which is about 23–46 $\mu$g/ml. Little or no slime is produced when S. epidermidis is grown in this medium.

Polysaccharides can be extracted from both the cells and the supernatant of clinical isolates of S. epidermidis grown on Columbia broth. In an initial step, the cultures are centrifuged and the cells and supernatants are pooled.

The polysaccharide can be extracted from the supernatant by concentrating the supernatant, washing it with water and then sequentially concentrating it. The final precipitate is dissolved in water, dialyzed and lyophilized.

To extract the polysaccharide from the cells, they are first disrupted with enzymes, lysostaphin or lysozyme, and then centrifuged. The supernatant is precipitated and then centrifuged. The supernatant is sequentially concentrated, incubated and then pelleted by centrifugation. The pellet is redissolved in water, dialyzed and lyophilized.

Alternatively, the lyophilized material is extracted with trichloroacetic acid and then centrifuged. Sequential precipitation with ethanol is followed by dissolution in distilled water, dialysis and lyophilization.

The crude extracts from cells and supernatants are further processed. In each case, the lyophilized material is dissolved in buffer and loaded on a separatory column equilibrated with the same buffer. The column is washed with loading buffer and then eluted with a salt gradient. The fractions containing antigen are pooled, concentrated, dialyzed and lyophilized. The separation can be repeated to obtain better purification. The purified polysaccharide can be sized on a suitable column and the fractions then pooled, concentrated, dialyzed and lyophilized.

The predominant serotypes for S. epidermidis are initially identified by selecting two isolates from a groups of about five to ten S. epidermidis isolates obtained from hospitals in various geographic locations. Rabbit antisera is produced with each of these two isolates, using an immunization scheme such as that described in McCarty and Lancefield is used. J. Exp. Med. 102:11–28 (1955). The antisera are absorbed with a non-encapsulated S. epidermidis strain. If necessary, additional absorptions can be performed to insure the removal of activity against other serotypes.

The two antisera are used to type the other, non-selected, isolates of S. epidermidis. If the first two isolates selected are of the same type, as evidenced by identical reactivity patterns with the other isolates, an additional isolate is selected from the group of isolates which did not react with the first two selected isolates. Rabbit antisera is produced against this isolate, which is then tested for reaction with the remaining isolates. This process is continued until the predominant serotypes to S. epidermidis are identified. Surprisingly, it is found that about 85% of clinical cases of S. epidermidis fall into one of two serotypes, denoted Type I and Type II.

For subsequent serotyping, type-specific polyclonal antibodies are prepared from rabbits immunized with a whole-cell vaccine produced from an identified Type I or Type II isolate, respectively. Representative Type I and Type II S. epidermidis organisms have been deposited with the American Type Culture Collection in Rockville, Md. and have been given accession numbers 55254 and 55253, respectively. Classification of isolates into serotypes can be performed using antisera to Type I and Type II isolates by bacterial agglutination assays as previously described for S. aureus. Nelles et al., Infect. Immun. 46:14–18 (1985).

For serological typing, cells are grown on Columbia broth under $CO_2$ tension. The cells are removed from the plates into phosphate-buffered saline (PBS). Protease is added to disrupt the resulting somewhat sticky suspension, producing an even cell suspension. Following enzymatic disruption, the polysaccharide capsules are fixed to the cell surface in preparation for agglutination assays. The fixed cells are centrifuged and resuspended in fresh PBS. They are then serotyped with antisera to Type I or Type II on a microtiter plate or in an agglutination test on a glass slide.

Each of the Type I and Type II serotypes has a specific surface antigen associated with it. These surface antigens are recognized by the rabbit antisera. A certain percentage of isolates are nontypable relative to the subset of antisera produced against Type I and Type II isolates.

The surface antigens associated with Type I and Type II are not present in non-encapsulated isolates which instead are covered by teichoic acid. They can be removed or disrupted by autoclaving, causing loss of reactivity with the specific antisera. Surface antigen for Type I does not cross-react with surface antigen for Type II, and vice versa.

In vitro phagocytosis assays indicate that antibodies to each of these surface antigens are protective against infection to the strains of *S. epidermidis* of the corresponding serotype. A vaccine based on these two serotypes can be used to protect against infection from the majority of clinical *S. epidermidis* strains.

Polysaccharides themselves are generally poor T-cell independent immunogens in humans, especially in patients with reduced resistance. It is therefore preferable to conjugate the polysaccharide to an immunocarrier, usually a polypeptide or protein, which is critical for the efficient interaction between T and B cells for the induction of an immune response against a weak immunogen. An immunocarrier thus enhances immunogenicity both for active immunization and for preparing high-titered antisera in volunteers for passive immunization. Particularly preferred immunocarriers according to the present invention include tetanus toxoid, diphtheria toxoid, *Pseudomonas aeroginosa* Exotoxin A or it derivatives, and other proteins commonly used as immunocarriers. Both Type I and Type II surface antigens can be bonded to the same immunocarrier.

The present invention also relates to the use of the polysaccharides corresponding to the two serotypes to produce antisera or monoclonal antibodies (mouse or human) that bind to or neutralize bacteria having these serotypes. Protocols for producing these antibodies are described in Ausubel, et al. (eds.), Chapter 11; in METHODS OF HYBRIDOMA FORMATION 257–71, Bartal & Hirshaut (eds.), Humana Press, Clifton, N.J. (1988); in Vitetta et al., *Immunol. Rev.* 62: 159–83 (1982); and in Raso, *Immunol. Rev.* 62: 93–117 (1982).

Inocula for polyclonal antibody production are typically prepared by dispersing the polysaccharide-immunocarrier in a physiologically-tolerable diluent such as saline or other adjuvants suitable for human use, to form an aqueous composition. An immunostimulatory amount of inoculum is administered to a mammal and the inoculated mammal is then maintained for a time period sufficient for the polysaccharide surface antigen to induce protecting anti-Type I or anti-Type II antibodies.

Antibodies can include antiserum preparations from a variety of commonly used animals, e.g., goats, primates, donkeys, swine, rabbits, horses, hens, guinea pigs, rats or mice, and even human antisera after appropriate selection and purification. The animal antisera are raised by inoculating the animals with formalin-killed Type I or Type II *S. epidermidis*, by conventional methods, bleeding the animals and recovering serum.

The antibodies induced in this fashion can be harvested and isolated to the extent desired by well known techniques, such as by immunoaffinity chromatography; that is, by binding antigen to a chromatographic column packing like Sephadex™, passing the antiserum through the column, thereby retaining specific antibodies and separating out other immunoglobulins and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the serum of patients having developed an antibody titer against the pathogen in question, thus assuring the retention of antibodies that are capable of binding to the surface antigens. They can then be used in preparations for passive immunization against *S. epidermidis*.

A monoclonal antibody composition contains, within detectable limits, only one species of antibody combining site capable of effectively binding to the polysaccharide surface antigen associated with either Type I or Type II. Suitable antibodies in monoclonal form can be prepared using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with a polypeptide of this invention. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred myeloma being P3X63-Ag8.653. The preferred fusion partner for human monoclonal antibody production is SHM-D33, a heteromyeloma available from ATCC, Rockville, Md. under the designation CRL 1668.

A monoclonal antibody composition of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal essential medium supplemented with 4.5 g/l glucose, 20 mm glutamine, and 20% fetal calf serum. An exemplary inbred mouse strain is the Balb/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the Type I and Type II surface antigens. More preferable in this regard, however, is a process that does not entail the use of a biological sample from an infected human subject. For example, a subject immunized with a vaccine as described herein can serve as a source for antibodies suitably used in an antibody composition within the present invention.

In a particularly preferred embodiment, monoclonal antibodies are produced to the Type I and Type II surface antigens using methods similar to those described for type-specific monoclonal antibodies to *S. aureus*. The purified monoclonal antibodies are characterized by bacterial agglutination assays using a collection of clinical isolates.

The monoclonal and polyclonal antibody compositions produced according to the present description can be used to induce an immune response for the prevention or treatment of Type I or Type II *S. epidermidis* infection. In this regard, the antibody preparation can be a polyclonal composition. Such a polyclonal composition can include antibodies that bind to both Type I and Type II, or it can include antibodies that bind only one of the two types. The polyclonal antibody component can be a polyclonal antiserum, preferably affinity purified, from an animal which has been challenged with both Type I and Type II surface antigens and, hence, stimulated to produce specific antibodies to both Type I and Type II surface antigens. Another alternative is to use an "engineered polyclonal" mixture, which is a mixture of monoclonal antibodies to Type I surface antigen and monoclonal antibodies to Type II surface antigen.

In both types of polyclonal mixtures, it can be advantageous to link polyspecific antibodies together chemically to form a single polyspecific molecule capable of binding to either surface antigen. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, LABELED ANTIBODIES IN BIOLOGY AND MEDICINE 321–23, McGraw-Hill Int'l Book Co. (1978); Nisonoff, et al., *Arch Biochem. Biophys.* 93: 470 (1961); and Hammerling, et al., *J. Exp. Med.* 128: 1461 (1968); and in U.S. Pat. No. 4,331,647.

An antibody component produced in accordance with the present invention can include whole antibodies, antibody fragments, or subfragments. Antibodies can be whole immunoglobulin (IgG) of any class, e.g., IgG, IgM, IgA, IgD, IgE, chimeric antibodies or hybrid antibodies with dual surface antigen specificity, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like *E. coli.* A lambda vector system is available thus to express a population of Fab's with a potential diversity equal to or exceeding that of subject generating the predecessor antibody. See Huse, W. D., et al., *Science* 246: 1275–81 (1989).

The acidic polysaccharide antigen associated with Type I and/or Type II can be the active ingredient in a composition, further comprising a pharmaceutically-acceptable carrier for the active ingredient, which can be used as a vaccine to induce a cellular immune response and/or production in vivo of antibodies which combat *S. epidermidis* infection. In this regard, a pharmaceutically-acceptable carrier is a material that can be used as a vehicle for administering a medicament because the material is inert or otherwise medically acceptable, as well as compatible with the polypeptide active agent, in the context of vaccine administration. In addition to a suitable excipient, a pharmaceutically-acceptable carrier can contain conventional vaccine additives like diluents, adjuvants, antioxidants, preservatives and solubilizing agents.

Pursuant to the present invention, such a vaccine can be administered to a subject not already infected with *S. epidermidis,* thereby to induce a response (humoral or cellular) to the corresponding serotypes of the bacteria in that subject. Alternatively, a vaccine within the present invention can be administered to a subject in which *S. epidermidis* infection has already occurred but is at a sufficiently early stage that antibodies produced in response to the vaccine effectively inhibit further spread of infection.

By another approach, a vaccine of the present invention can be administered to a subject who then acts as a source for globulin, produced in response to challenge from the specific vaccine ("hyperimmune globulin"), that contains antibodies directed against *S. epidermidis.* A subject thus treated would donate plasma from which hyperimmune globulin would then be obtained, via conventional plasma-fractionation methodology, and administered to another subject in order to impart resistance against or to treat *S. epidermidis* infection.

Induction of bacteremia in mammals requires extremely high numbers of organisms or some previous maneuver to lower the host resistance. In vitro phagocytosis, however, can be studied as a correlate of protective immunity in vivo. In this model, the ability of the type-specific monoclonal and polyclonal antibodies to opsonize *S. epidermidis* in vitro is measured by phagocytosis, according to the method described in Kojima et al., *J. Infect Dis.* 162: 435–551 (1990) and Fattom, et al., *Infect. Immun.* 58: 2367–2374 (1990). Antibodies induced by Type I and Type II vaccines facilitate type-specific phagocytosis.

The present invention is further described by reference to the following, illustrative examples.

EXAMPLE 1

Collection of *S. epidermidis* Strains

Clinical isolates of *S. epidermidis* were obtained from hospitals in various geographic locations. The isolates were all blood isolates. Identification of the isolates as *S. epidermidis* was confirmed. In most cases, the hospital provided a synopsis of the infection episode and outcome of treatment, as well as results of biochemical identification and antimicrobial sensitivity determinations.

EXAMPLE 2

Culture of *S. epidermidis* Strains

The isolates were grown on plates of Columbia agar (Difco), supplemented with 4% NaCl, at 37° C. under $CO_2$ tension. An isolated colony was removed into a 500 ml flask containing Columbia Broth (Difco), supplemented with 4% NaCl. After growing for three to five hours, each of six two-liter Fernbach flasks containing 1.2 liters of Columbia salt broth were inoculated with 50 mL of the starter. The Fernbach flasks were grown on a New Brunswick shaker overnight at 37° C. The cells were harvested by centrifugation at 10,000 g for 30 minutes and the supernatants and cells were pooled.

EXAMPLE 3

Identification of Predominant Serotypes of *S. epidermidis.*

Five to ten *S. epidermidis* isolates are obtained from various hospitals, grown in Columbia broth and harvested as in Example 2. Cells from two of the isolates are fixed with 1% formalin. The immunization scheme of McCarty and Lancefield, supra, is used to produce rabbit antisera specific to each of the selected isolates. The antisera are absorbed with a non-encapsulated *S. epidermidis* strain. If necessary, additional absorptions are performed to insure the removal of activity against other serotypes.

The two antisera are used to type the other, non-selected, isolates of *S. epidermidis.* If the first two isolates selected are of the same type, as evidenced by identical reactivity patterns with the other isolates, an additional isolate is selected from the group of isolates which did not react with the first two selected isolates. Rabbit antisera is produced against this isolate, which is then tested for reaction with the remaining isolates. This process is continued until the two most predominant serotypes to *S. epidermidis* are identified. These two serotypes account for approximately 85% of the clinical isolates. (See Table 1 in Example 7.)

EXAMPLE 4

Preparation of Type I and Type II Specific Rabbit Antisera

Purified acidic polysaccharide antigens were obtained from *S. epidermidis* identified as being either Type I or Type II and were grown in Columbia broth and harvested as in Example 2. The cells were fixed with 1% formalin. The immunization scheme of McCarty and Lancefield, supra, was used to produce rabbit antisera specific to each of Type I and Type II. The antisera were absorbed with a non-encapsulated *S. epidermidis* strain.

EXAMPLE 5

Extraction of *S. epidermidis* Type I and Type II Polysaccharides

From the supernatant:

The supernatant was concentrated, washed with distilled water and sequentially precipitated with 25% ethyl alcohol supplemented with 5–10 mM $CaCl_2$ at 4° C. for six hours overnight. After centrifuging, the supernatant was precipitated in 75% ethyl alcohol supplemented with 5–10 mM $CaCl_2$. The 75% precipitate was dissolved in distilled water, dialyzed against distilled water overnight and then lyophilized.

From the cells:

The cells were disintegrated with enzymes, lysostaphin or lysozyme, or were extracted with 5% trichloroacetic acid at 4° C. for two to three days. The cells were then centrifuged at 10,000 g for 30 minutes. The supernatant was precipitated with 25% ethyl alcohol supplemented with 5–10 mM $CaCl_2$ at 4° C. overnight. After centrifugation, the supernatant was precipitated with 75% ethyl alcohol supplemented with 5–10 mM $CaCl_2$. After incubation at 4° C. overnight, the precipitate was pelleted by centrifuging at 10,000 g for 30 minutes, redissolved in distilled water, dialyzed against distilled water overnight and then lyophilized.

EXAMPLE 6

Purification of *S. epidermidis* Type I and Type II Surface Antigens

The crude lyophilized extracts from Example 5 were dissolved in 0.05 sodium acetate buffer at pH 6.0 to a final concentration of 50–100 mg/mL. If the crude extract is highly contaminated with nucleic acids and/or proteins, it may be pretreated with RNAse, DNAse and/or protease, before further processing. The dissolved crude extract was loaded on a DEAE sepharose column equilibrated in the same buffer at about 10 mg/mL gel. After washing the column with the loading buffer until no absorption at 206 nm was observed, the column was eluted with NaCl gradient 0–0.3M in 0.05M sodium acetate buffer at pH 6.0. Immunoprecipitation using type-specific antisera prepared according to Example 4 was used to identify fractions containing antigen. The Type I and Type II antigens elute at the same molarity as known Staphylococcus aminouronic acid polymers. Acid hydrolysis of purified Type I and Type II antigens also indicate that they comprise aminouronic acids.

The fractions containing antigen were pooled, concentrated on an ultrafiltration Amicon membrane, dialyzed against distilled water four times and lyophilized. This procedure was repeated when better purification of the antigen was desired. The purified polysaccharide was sized on a gel filtration column such as a sepharose 6B column or Sephacryl S-300 column. The antigen elutes in the same position as the capsular antigen of Type 5 and Type 8 antigens from *S. aureus*. The polysaccharide fractions were pooled, concentrated on an ultrafiltration Amicon membrane, dialyzed against distilled water and lyophilized. The result of this purification is Type I or Type II antigen in substantially pure form.

Protein and nucleic acid analysis of the purified Type I and Type II antigens revealed that neither antigen contains protein or nucleic acids. Trypsin hydrolysis revealed that Type I and Type II antigens are trypsin resistant. When cells were heat treated at 100° C. for thirty minutes, the surface antigens were selectively removed, i.e., teichoic acid was not removed. Before heat treatment, the cells did not react with anti-teichoic acid antiserum, whereas after heat treatment, the cells did react.

EXAMPLE 7

Serotyping of Clinical Isolates

Clinical isolates grown in Columbia broth or on Columbia agar plates, as described in Example 2, were fixed with 1% formalin. If the isolates were grown on agar plates, the cells were first scraped from the plates, suspended in PBS and supplemented with 20–50 micrograms/mL of protease. If the cells were grown in Columbia broth, they were resuspended in PBS, and supplemented with 20–50 micrograms/mL of protease. The cells were diluted in PBS to an optical density of 0.5. The mixture was incubated at 37° C. for one hour and then fixed with 1% formalin at room temperature overnight. The cells were washed with PBS and slide agglutination was performed in 96-well microtiter plates or on a glass slide with the suspension of the formalin-fixed cells. Equal volumes of cells and antiserum prepared according to Example 4 were mixed and allowed to agglutinate in the microtiter plate. Alternatively, cells and antiserum prepared according to Example 4 were mixed in equal volumes on a glass slide, and rotated for several minutes. The presence or absence of agglutination was scored.

Serotyping results for confirmed bacteremic isolates from different geographical locations in the United States are shown in Table 1. A certain percentage of isolates are nontypable (NT).

TABLE 1

| Source | Type I | Type II | NT | Total |
| --- | --- | --- | --- | --- |
| Wash. DC | 16 (41%) | 21 (54%) | 2 (5%) | 39 (100%) |
| Maryland | 4 (8%) | 28 (62%) | 13 (29%) | 45 (100%) |
| Tennessee | 0 (0%) | 12 (92%) | 1 (8%) | 13 (100%) |
| London | 9 (23%) | 27 (69%) | 3 (7%) | 39 (100%) |
| Mass. | 1 (10%) | 8 (80%) | 1 (10%) | 10 (100%) |
| Total | 30 (20%) | 96 (66%) | 20 (14%) | 146 (100%) |

EXAMPLE 8

Production of Polyclonal and Monoclonal anti-*S. epidermidis* Antibodies

BALB/c mice are immunized with formalin-fixed bacteria. Sera are obtained and screened for a type-specific response by a bacterial agglutination assay as described in Example 7. Upon evidence of a hyperimmune response, the mice are immunized three days prior to fusion. Spleen cells from the immune mice are fused to cells from the AG653 cell line or SHM D33 (both available from ATCC, Rockville, Md.), or a clone or subclone of one of these cell lines, using the method described in Fuller et al., CURRENT PROTOCOLS IN MOLECULAR BIOLOGY, New York: J. Wiley and Sons (1989), Chapters 11.3.2–11.11.4. Hybridomas are screened for type-specific antibody by bacterial agglutination assay and ELISA using microtiter plates coated with either formalin-fixed whole bacteria or purified cell surface components. Cells from positive wells are cloned by limiting dilution. Milligram quantities of antibody are prepared in ascites fluids and purified by protein A, protein G or DEAE sepharose column chromatography.

EXAMPLE 9

In Vitro Phagocytosis Assay

Polymorphonuclear neutrophils (PMNs) and monocytes are prepared from peripheral human blood. The PMNs and monocytes are resuspended in RPMI (Gibco), or similar cell culture medium, with 5% heat-inactivated fetal calf serum. S. epidermidis cells grown in Columbia broth will be washed and added to either PMNs or monocytes along with the test antibody. After incubation at 37° C. with gentle rotation, samples are removed at times 0, 60 and 120 minutes after incubation and spread onto Columbia salt agar plates. After overnight incubation at 37° C. the number of colonies is determined.

What is claimed is:

1. A vaccine comprising a sterile, pharmaceutically-acceptable carrier and a composition consisting essentially of a polysaccharide antigen that is obtained by a process comprising steps of:

growing cells of a Type I isolate of S. epidermidis that agglutinates antisera to ATCC 55254;

extracting polysaccharide antigen from said cells to produce a crude extract of Type I polysaccharide antigen;

purifying said crude extract to produce purified antigen that contains less than 1% protein;

loading said purified antigen on a separatory column and eluting it with a NaCl gradient; and identifying fractions containing Type I polysaccharide antigen using antibodies specific to a Type I isolate.

2. A vaccine according to claim 1, wherein said NaCl gradient is 0–0.3M.

3. A vaccine according to claim 1, wherein said step of extracting said polysaccharide antigen in the process of making said composition comprises treatment with trichloroacetic acid.

4. A vaccine according to claim 1, wherein said step of extracting said polysaccharide antigen in the process of making said composition comprises treatment with 5% trichloroacetic acid at 4° C.

5. A vaccine according to claim 1, wherein said step of extracting said polysaccharide antigen in the process of making said composition comprises treatment with enzymes.

6. A vaccine according to claim 1, wherein said step of extracting said polysaccharide antigen in the process of making said composition comprises treatment with lysostaphin or lysozyme.

7. A vaccine according to claim 1, additionally comprising a step of treating said crude extract with protease.

8. A vaccine according to claim 1, wherein said cells are grown in Columbia broth.

9. A vaccine according to claim 1, wherein said step of identifying fractions containing said Polysaccharide antigen in the process of making said composition comprises immunoprecipitation.

10. A vaccine according to claim 1, wherein the process of making said composition additionally comprises a step of sequentially precipitating said crude extract with 25–75% ethyl alcohol.

* * * * *